(12) United States Patent
Yong et al.

(10) Patent No.: US 11,707,604 B2
(45) Date of Patent: Jul. 25, 2023

(54) PRIMER FOR INTRAVENOUS CATHETER SYSTEMS

(71) Applicant: Becton, Dickinson and Company, Franklin Lakes, NJ (US)

(72) Inventors: Zhee Min Jimmy Yong, Singapore (SG); Chun Keat Ooi, Limerick (IE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 316 days.

(21) Appl. No.: 17/207,457

(22) Filed: Mar. 19, 2021

(65) Prior Publication Data

US 2021/0299408 A1    Sep. 30, 2021

Related U.S. Application Data

(60) Provisional application No. 63/002,866, filed on Mar. 31, 2020.

(51) Int. Cl.
*A61M 25/06* (2006.01)
*A61M 39/10* (2006.01)
*A61M 1/36* (2006.01)

(52) U.S. Cl.
CPC ...... *A61M 25/0606* (2013.01); *A61M 1/3643* (2013.01); *A61M 39/10* (2013.01); *A61M 2039/1077* (2013.01)

(58) Field of Classification Search
CPC ............ A61M 25/0606; A61M 1/3643; A61M 39/10; A61M 2039/1077

USPC ......................................................... 604/122
See application file for complete search history.

(56) References Cited

U.S. PATENT DOCUMENTS

2017/0258991 A1 * 9/2017 Tornblom ........... A61M 5/1407
2020/0023176 A1    1/2020 Hu et al.

FOREIGN PATENT DOCUMENTS

WO      2016/037646         3/2016
WO  WO-2016037646 A1 *  3/2016  .......... A61M 39/223

* cited by examiner

*Primary Examiner* — Phillip A Gray
(74) *Attorney, Agent, or Firm* — Kirton McConkie; Whitney Blair; Kevin Stinger

(57) ABSTRACT

A primer may be used with IV catheter systems. The primer may be positioned along the tubing of an extension set such that the primer divides the IV catheter system into a downstream portion and an upstream portion. The primer may vent air from both the upstream and downstream portions to allow blood to flow up to the primer while also allowing priming solution to flow down to the primer. As a result, the catheter may be inserted into the patient's vasculature without first priming the catheter. Once the air has been vented from the upstream and downstream portions of the IV catheter system, the primer may be actuated to open a fluid pathway through the primer. With the fluid pathway opened, the priming solution may commence flowing towards the patient's vasculature thereby flushing the blood from the IV catheter system.

20 Claims, 8 Drawing Sheets

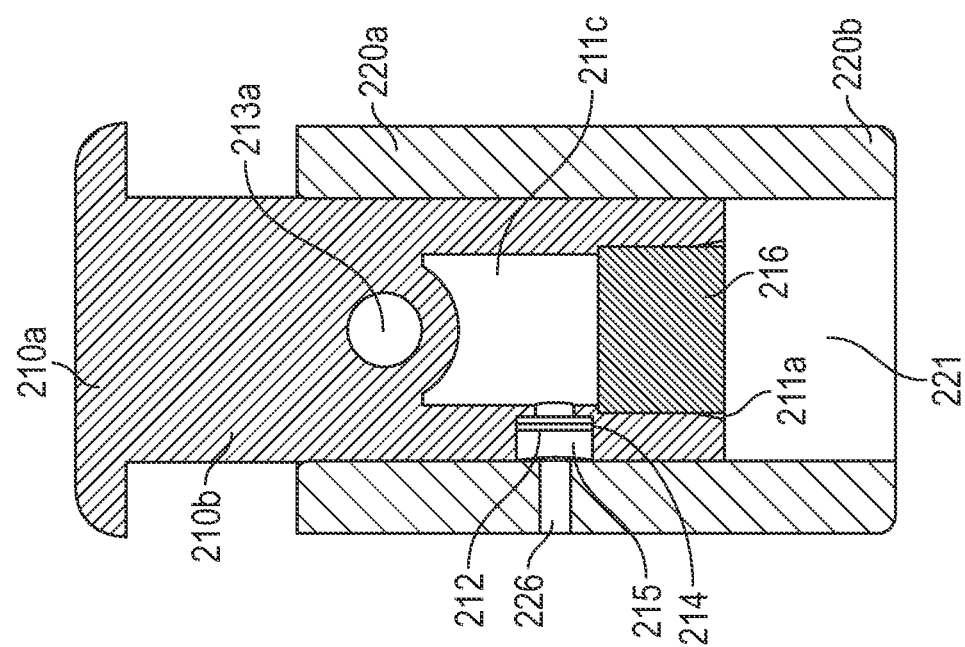
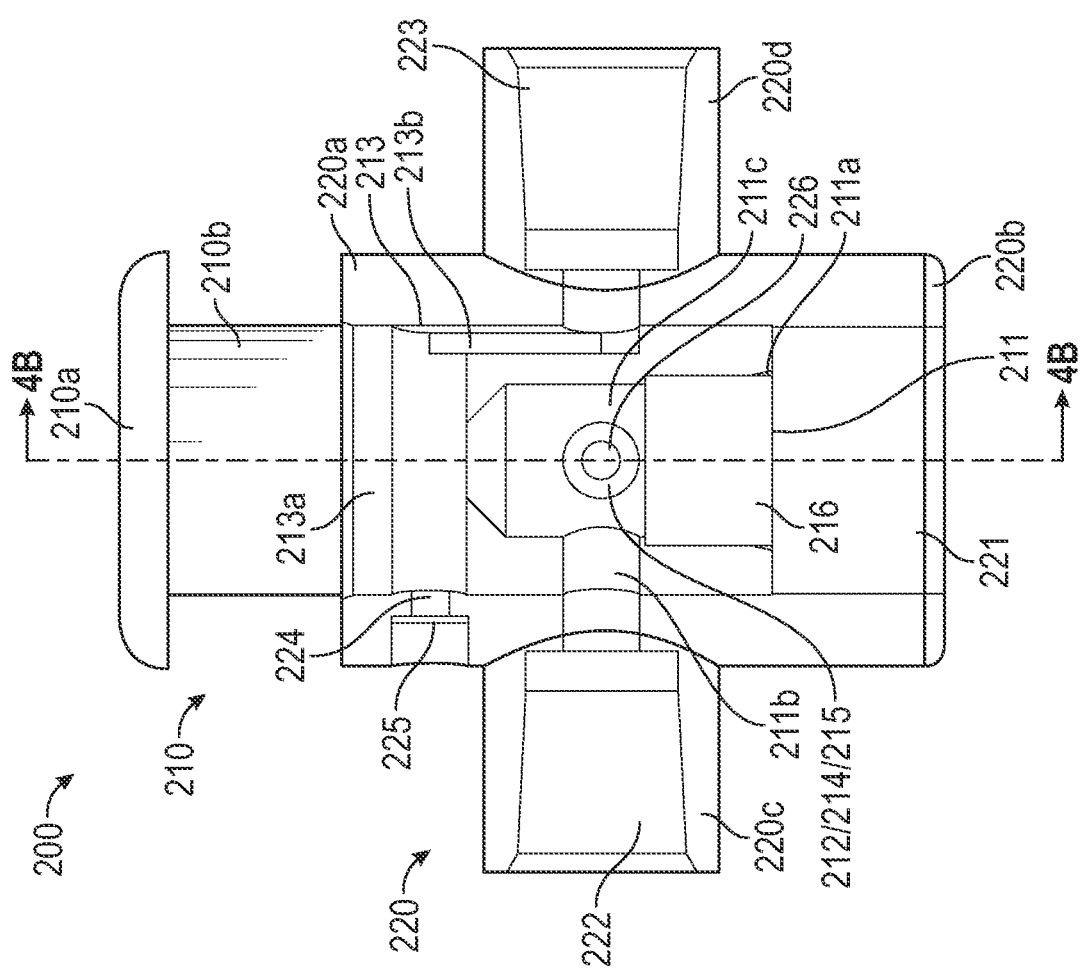
FIG. 4B
FIG. 4A

PRIMER FOR INTRAVENOUS CATHETER SYSTEMS

RELATED APPLICATIONS

This application claims the benefit of U.S. Provisional Patent Application No. 63/002,866, filed on Mar. 31, 2020, entitled PRIMER FOR INTRAVENOUS CATHETER SYSTEMS, which is incorporated herein in its entirety.

BACKGROUND

Intravenous (IV) catheter systems are commonly used for a variety of infusion therapies. For example, an IV catheter system may be used for infusing fluids, such as normal saline solution, various medicaments, and total parenteral nutrition, into a patient. IV catheter systems may also be used for withdrawing blood from the patient.

A common type of IV catheter system is an over-the-needle peripheral intravenous ("IV") catheter ("PIVC"). As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into the vasculature of the patient.

An integrated IV catheter system (such as an integrated PIVC) is an IV catheter system having an integrated extension set. Such extension sets typically consist of extension tubing that is integrated at one end into the catheter adapter and that includes an access port (e.g., a luer connector) coupled to the other end. Integrated PIVCs are oftentimes used to draw blood. For example, after inserting the catheter of the integrated PIVC into the patient's vasculature, a clinician may allow blood to flow into the extension set up to the access port. Once the blood has flowed up to the access port, the clinician may attach a blood collection set (e.g., a vacuum tube adapter) to the access port to collect a blood sample. During this process, it is possible that blood will leak out from the access port. Also, with some integrated IV catheter systems, it is necessary to prime the catheter before inserting it into the patient's vasculature.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a primer that may be used with IV catheter systems and related methods. In some embodiments, the primer may be positioned along the tubing of an extension set such that the primer divides the IV catheter system into a downstream (or distal) portion and an upstream (or proximal) portion. In some embodiments, the primer vents air from both the upstream and downstream portions to allow blood to flow up to the primer while also allowing priming solution to flow down to the primer. As a result, the catheter may be inserted into the patient's vasculature without first priming the catheter. In some embodiments, once the air has been vented from the upstream and downstream portions of the IV catheter system, the primer may be actuated to open a fluid pathway through the primer. In some embodiments, with the fluid pathway opened, the priming solution may commence flowing towards the patient's vasculature thereby flushing the blood from the IV catheter system.

In some embodiments, the present disclosure relates to a primer for an intravenous catheter system. In some embodiments, the primer may include a main body forming a plunger channel and having a distal end that forms a distal channel that connects to the plunger channel and a proximal end that forms a proximal channel that connects to the plunger channel. In some embodiments, the main body may include a venting channel, which may extend between the plunger channel through an exterior surface of the main body. In some embodiments, the primer may include a plunger having a plunger main body that inserts into and slides within the plunger channel between a closed position and an open position. In some embodiments, the plunger main body may include a first channel and a second channel. In some embodiments, in response to the plunger being in the closed position, the first channel may connect the proximal channel to the venting channel to thereby vent air contained in extension tubing connected to the proximal end through the venting channel. In some embodiments, in response to the plunger being in the closed position, the second channel may be aligned with the distal channel to thereby vent air contained in extension tubing connected to the distal end through the second channel. In some embodiments, in response to the plunger being in the open position, the first channel may connect the proximal channel to the distal channel to thereby enable fluid flow through the primer.

In some embodiments, the first channel may include a primary channel that extends through the plunger main body and a branch channel that extends from the primary channel through a proximal exterior surface of the plunger main body. In some embodiments, in response to the plunger being in the closed position, the branch channel may align with the proximal channel, and the primary channel may align with the venting channel. In some embodiments, in response to the plunger being in the open position, the primary channel may align with the proximal channel and the distal channel.

In some embodiments, the second channel may include a horizontal channel that extends through a distal exterior surface of the plunger main body and a vertical channel that extends through a bottom exterior surface of the plunger main body. In some embodiments, in response to the plunger being in the closed position, the horizontal channel may align with the distal channel.

In some embodiments, the primer may include a first venting member positioned in the venting channel and a second venting member positioned in the second channel. In some embodiments, the first venting member and the second venting member may each include hydrophobic membranes, and the primer may include a hydrophilic membrane positioned in the second channel distal to the second venting member.

In some embodiments, the main body may include a second venting channel that extends from the plunger channel through the exterior surface of the main body. In some embodiments, the second channel may form a blood chamber, and the plunger main body may further include a third channel that extends from the blood chamber through an exterior surface of the plunger main body. In such embodiments, in response to the plunger being in the closed position, the third channel may align with the second venting channel such that the air contained in the extension tubing connected to the distal end is vented through the second channel, the third channel and the second venting channel.

In some embodiments, the second channel may be formed by a horizontal channel that extends through a distal exterior surface of the plunger main body and a vertical channel that extends through a bottom exterior surface of the plunger main body. In some embodiments, the blood chamber may be formed between the horizontal and vertical channels. In some embodiments, the primer may further include a septum positioned in the vertical channel between the blood chamber and the bottom exterior surface. In some embodiments, the primer may include a first venting member positioned in the venting channel and a second venting member positioned in the third channel. In some embodiments, the first and second venting members may each be hydrophobic membranes, and the primer may further include a hydrophilic membrane positioned in the third channel between the second venting member and the blood chamber.

In some embodiments, an intravenous catheter system may include one or more of the following: a catheter assembly having a catheter adapter and a catheter that extends distally from the catheter adapter; extension tubing that is fluidly coupled to the catheter adapter; an access port positioned at a proximal end of the extension tubing; and a primer. In some embodiments, the primer may be coupled inline to the extension tubing such that a distal portion of the extension tubing is positioned between the primer and the catheter adapter and a proximal portion of the extension tubing is positioned between the primer and the access port. In some embodiments, the primer may include a main body forming a plunger channel and including a distal end that is coupled to the distal portion of the extension tubing.

In some embodiments, the distal end may form a distal channel that connects to the plunger channel. In some embodiments, the main body may include a proximal end that that is coupled to the proximal portion of the extension tubing. In some embodiments, the proximal end may form a proximal channel that connects to the plunger channel. In some embodiments, the main body further may include a venting channel that extends between the plunger channel through an exterior surface of the main body.

In some embodiments, the primer may include a plunger, which may include a plunger main body that inserts into and slides within the plunger channel between a closed position and an open position. In some embodiments, the plunger main body may include a first channel and a second channel. In some embodiments, in response to the plunger being in the closed position, the first channel may connect the proximal channel to the venting channel to thereby vent air contained in the proximal portion of the extension tubing through the venting channel, and the second channel may be aligned with the distal channel to thereby vent air contained in distal portion of the extension tubing through the second channel. In some embodiments, when the plunger is in the open position, the first channel may connect the proximal channel to the distal channel to thereby enable fluid flow through the primer.

In some embodiments, the first channel may include a primary channel that extends through the plunger main body and a branch channel that extends from the primary channel through a proximal exterior surface of the plunger main body. In some embodiments, in response to the plunger being in the closed position, the branch channel may align with the proximal channel and the primary channel may align with the venting channel. In some embodiments, in response to the plunger being in the open position, the primary channel may align with the proximal channel and the distal channel. In some embodiments, the second channel may include a horizontal channel, which may extend through a distal exterior surface of the plunger main body, and a vertical channel, which may extend through a bottom exterior surface of the plunger main body.

In some embodiments, the main body may include a second venting channel that extends from the plunger channel through the exterior surface of the main body. In some embodiments, the second channel may form a blood chamber, and the plunger main body may include a third channel that extends from the blood chamber through an exterior surface of the plunger main body. In some embodiments, in response to the plunger being in the closed position, the third channel may align with the second venting channel such that the air contained in the distal portion of the extension tubing is vented through the second channel, the third channel and the second venting channel. In some embodiments, the primer may include a septum positioned in the second channel between the blood chamber and a bottom exterior surface of the plunger main body.

In some embodiments, the primer may include one or more of the following: a first venting member that vents the air contained in the proximal portion of the extension tubing; a second venting member that vents the air contained in the distal portion of the extension tubing; and a hydrophilic membrane that is positioned distal to the second venting member.

In some embodiments, a primer for an intravenous catheter system may include a main body and a plunger. In some embodiments, the main body may form a plunger channel. In some embodiments, the main body may include a distal end that forms a distal channel that connects to the plunger channel and a proximal end that forms a proximal channel that connects to the plunger channel. In some embodiments, the main body may include a venting channel that extends between the plunger channel through an exterior surface of the main body. In some embodiments, the primer may include a plunger, which may include a plunger main body that inserts into and slides within the plunger channel between a closed position and an open position.

In some embodiments, the plunger main body may include a first channel and a second channel. In some embodiments, the first channel may include a primary channel and a branch channel. In some embodiments, in response to the plunger being in the closed position, the branch channel may align with the proximal channel and the primary channel may align with the venting channel to thereby vent air contained in extension tubing connected to the proximal end through the venting channel. In some embodiments, the second channel may be aligned with the distal channel to thereby vent air contained in extension tubing connected to the distal end through the second channel. In some embodiments, in response to the plunger being in the open position, the primary channel may connect the proximal channel to the distal channel to thereby enable fluid flow through the primer.

It is to be understood that both the foregoing general description and the following detailed description are examples and explanatory and are not restrictive of the present disclosure, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present disclosure. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 4A is a front view of another example of a primer that configured for drawing a blood sample, illustrating the primer in the closed position, in accordance with some embodiments;

FIG. 4B is a cross-sectional view of the primer of FIG. 4A;

DESCRIPTION OF EMBODIMENTS

Embodiments of the present disclosure will primarily be described in the context of integrated PIVCs. However, embodiments of the present disclosure equally extend to other integrated IV catheter systems as well as to any vascular access device on which an embodiment of the described primers may be employed. For purposes of the specification and the claims, the term "integrated" in the context of an IV catheter system shall represent that the IV catheter system includes tubing that provides fluid access to the catheter (e.g., an "extension set"). The term "tubing" shall be construed as any elongated material that defines a fluid pathway.

Figure 1:
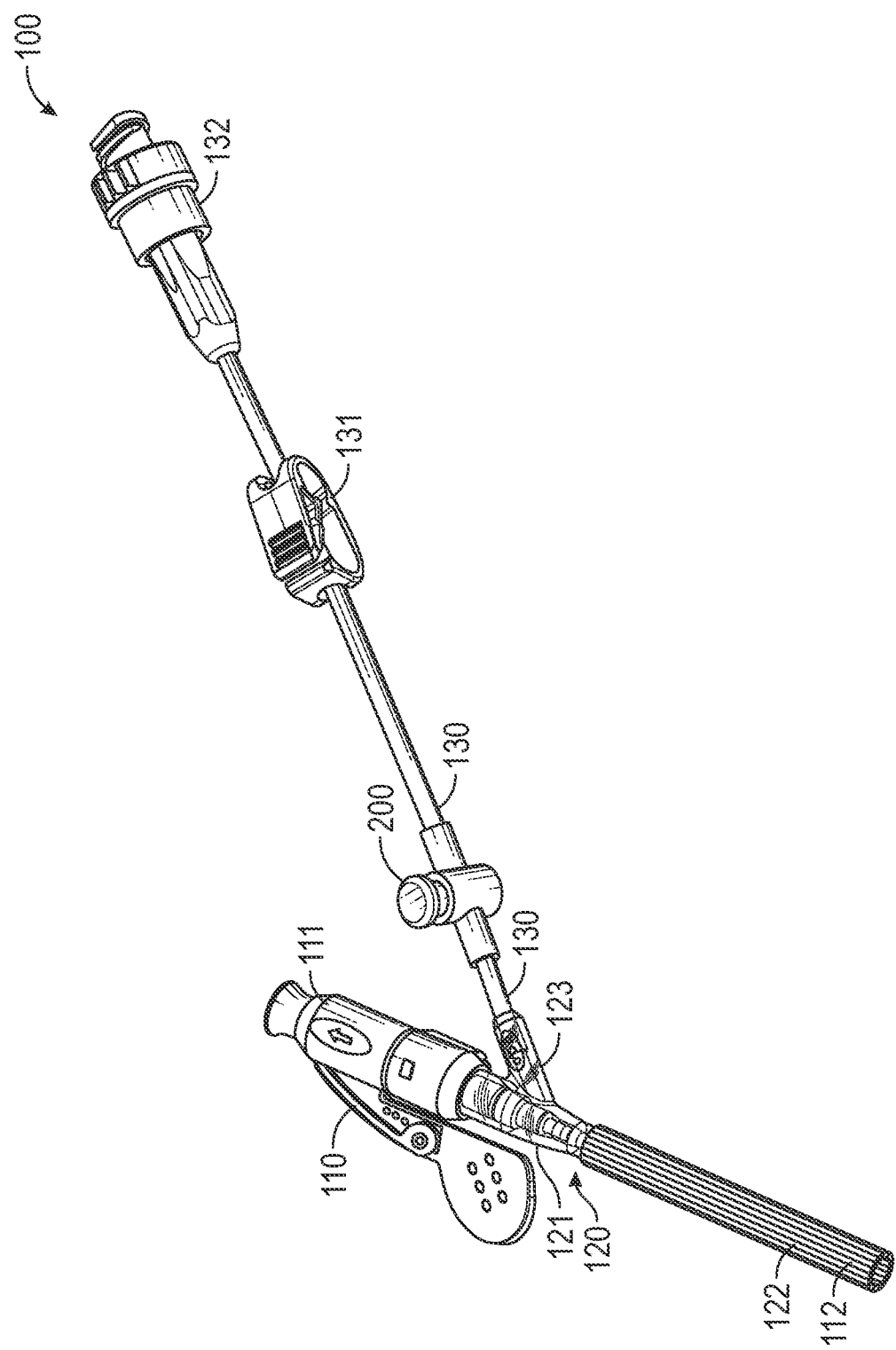
FIG. 1 is an upper perspective view of an example IV catheter system that includes a primer, in accordance with some embodiments.

FIG. 1 provides an example of an integrated PIVC 100 that includes a primer 200 that is configured in accordance with some embodiments. In some embodiments, the PIVC 100 may include a needle assembly 110 coupled to a catheter assembly 120. In some embodiments, the catheter assembly 120 may include a catheter adapter 121 from which a catheter 122 extends distally. In some embodiments, the needle assembly 110 may include a needle adapter 111 from which a needle 112 extends distally. In some embodiments, in response to the needle assembly 110 being coupled to catheter assembly 120, the needle 112 may extend through and distally beyond catheter 122. In some embodiments, a needle shield 113 may cover the needle 112 and the catheter 122 but would be removed prior to insertion of the needle and catheter.

In some embodiments, the catheter assembly 120 may include an extension port 123 that forms an opening into the lumens of the catheter adapter 121 and the catheter 122. In some embodiments, an access port 132 may be coupled to extension port 123 via extension tubing 130. In some embodiments, a primer 200 may be positioned inline with extension tubing 130. In other words, a portion of extension tubing 130 may be positioned distal (or downstream) to primer 200 and another portion of extension tubing 130 may be positioned proximal (or upstream) from primer 200. However, in some embodiments, primer 200 could couple directly to extension port 123. In some embodiments, one benefit of connecting primer 200 to extension port 123 via extension tubing 130 is that it will enable primer 200 to be moved relative to catheter adapter 121 due to the flexibility of extension tubing 130. In some embodiments, a pinch clamp 131 may also be attached to the portion of extension tubing 130 proximal to primer 200 and may be selectively clamped to block fluid from flowing through the tubing. In some embodiments, access port 132 may represent any of many different types of connectors that may be used on or connected to an extension set. In some embodiments, access port 132 may be used to connect a drip line to PIVC 100 but any fluid source could be connected to access port 132.

Figure 2A:
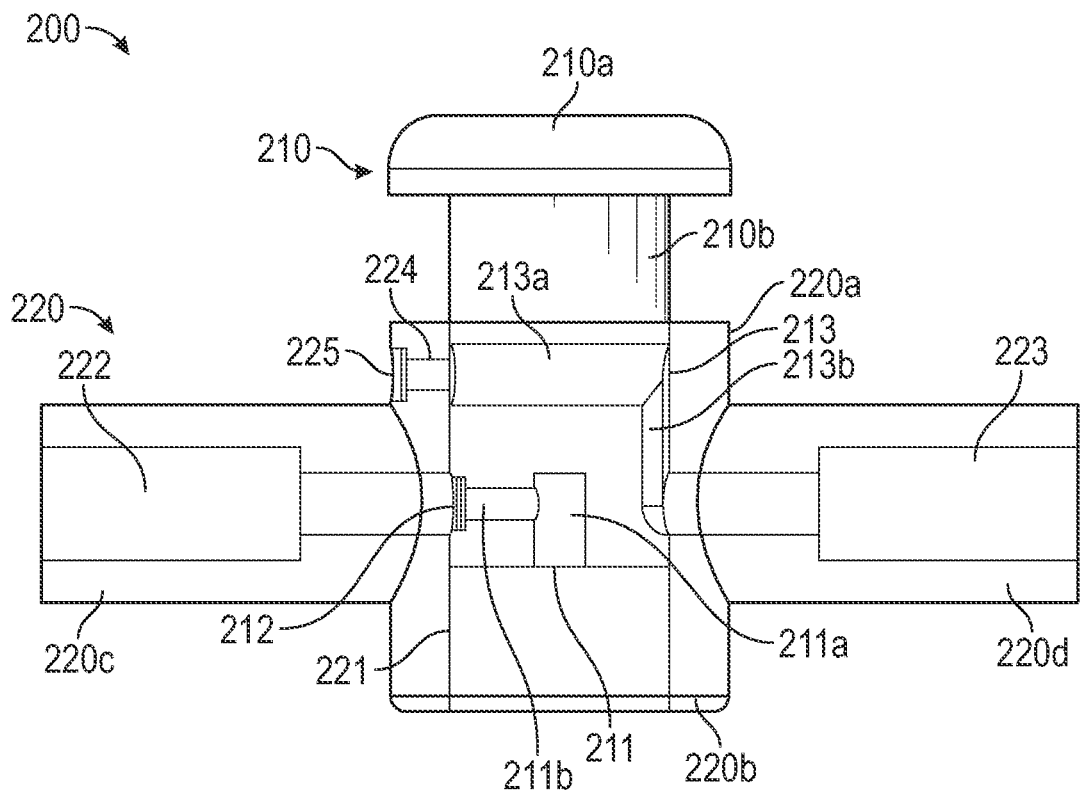
FIGS. 2A and 2B are front views of an example of a primer, illustrating the primer in the closed and open positions, respectively, in accordance with some embodiments.
Figure 2B:
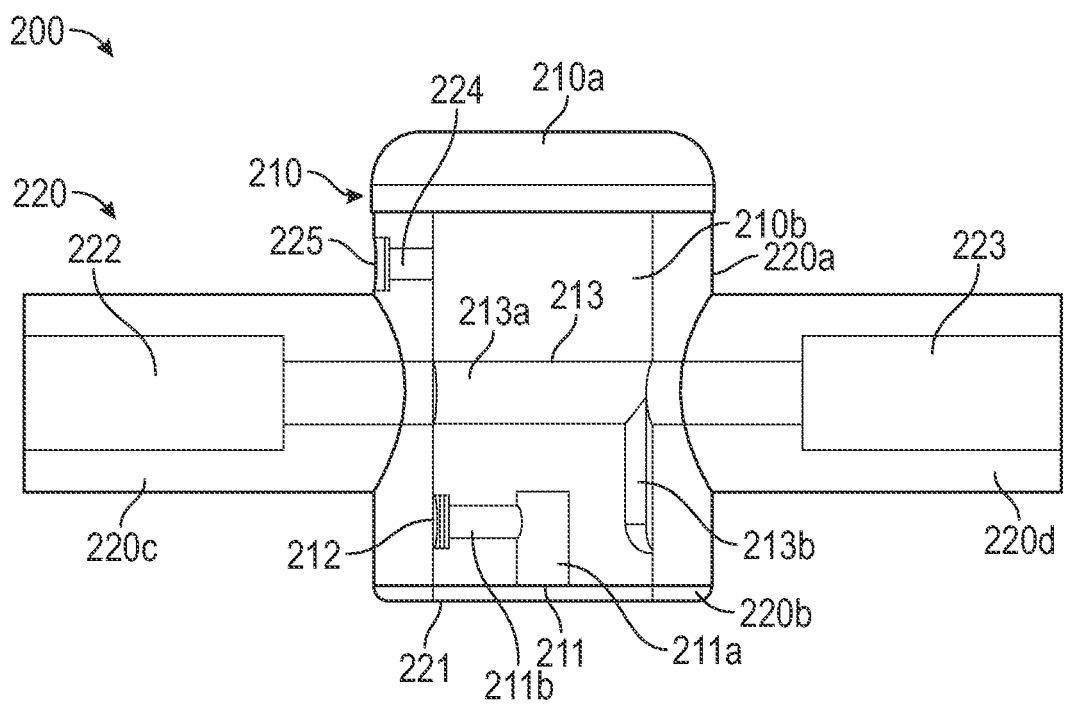
Figure 2C:
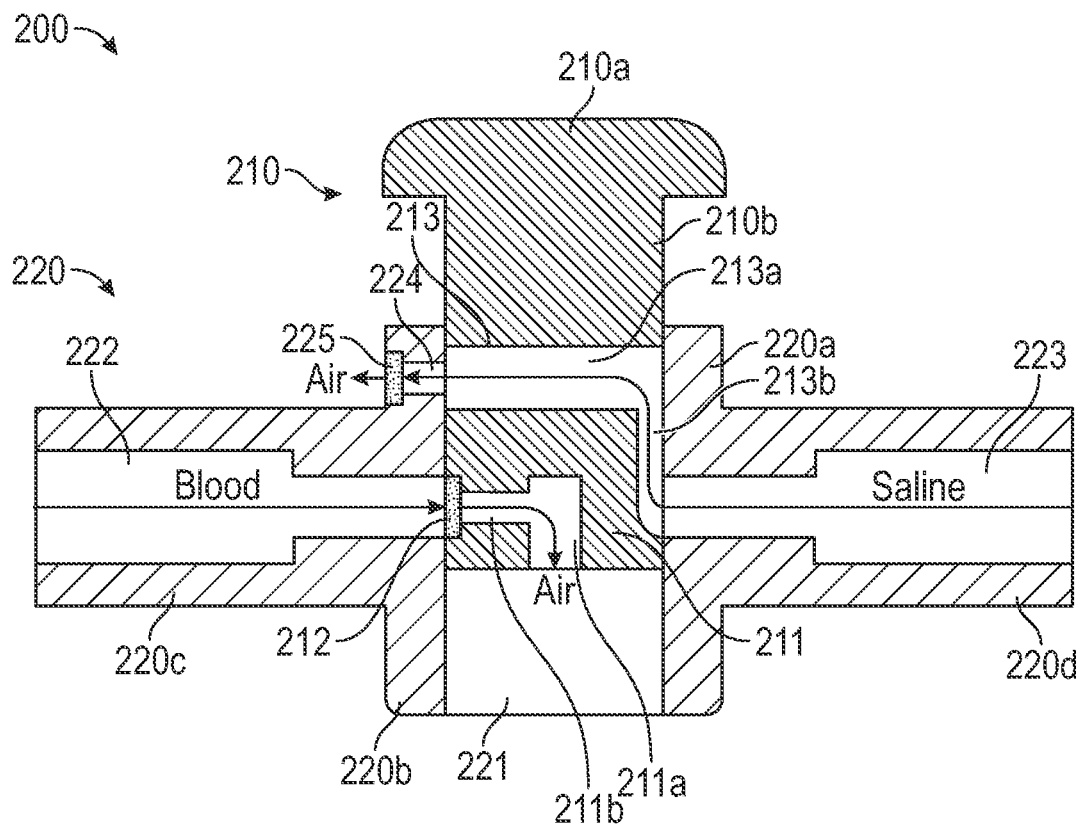
FIGS. 2C and 2D are cross-sectional views of the primer depicted in FIGS. 2A and 2B, respectively, in accordance with some embodiments.
Figure 2D:
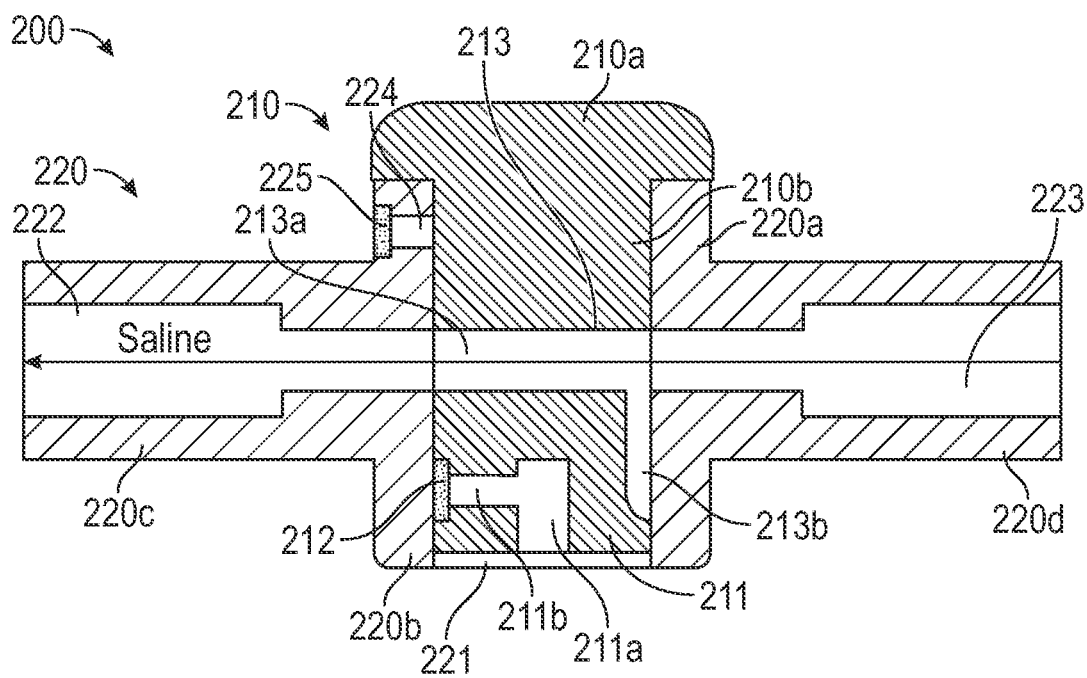

FIGS. 2A and 2B provide front views of an embodiment of primer 200. It is noted that, in these figures, primer 200 is shown as being transparent so that the internal structures may be visualized. FIGS. 2C and 2D provide cross-sectional front views of this embodiment of primer 200 to better illustrate the internal structures. In some embodiments, primer 200 may include a plunger 210 and a main body 220 into which plunger 210 inserts. In some embodiments, plunger 210 may move between a closed position as shown in FIG. 2A and an open position as shown in FIG. 2B. In some embodiments, when in the closed position, primer 200 vents air but blocks fluid flow, while in the open position, primer 200 allows fluid flow.

In some embodiments, main body 220 may include a top 220a, a bottom 220b, a distal end 220c and a proximal end 220d. The terms "top" and "bottom" are used only to distinguish the two opposing sides of primer 200 but should not be construed as requiring either side to be oriented in any particular direction. Likewise, the terms "horizontal" and "vertical" as used below are intended to distinguish between various components but should not be viewed as requiring such components to be in any particular orientation. Distal end 220c is the end of primer 200 that is closest to catheter adapter 121, while proximal end 220d is the end of primer 200 that is closest to access port 132.

Figure 2E:
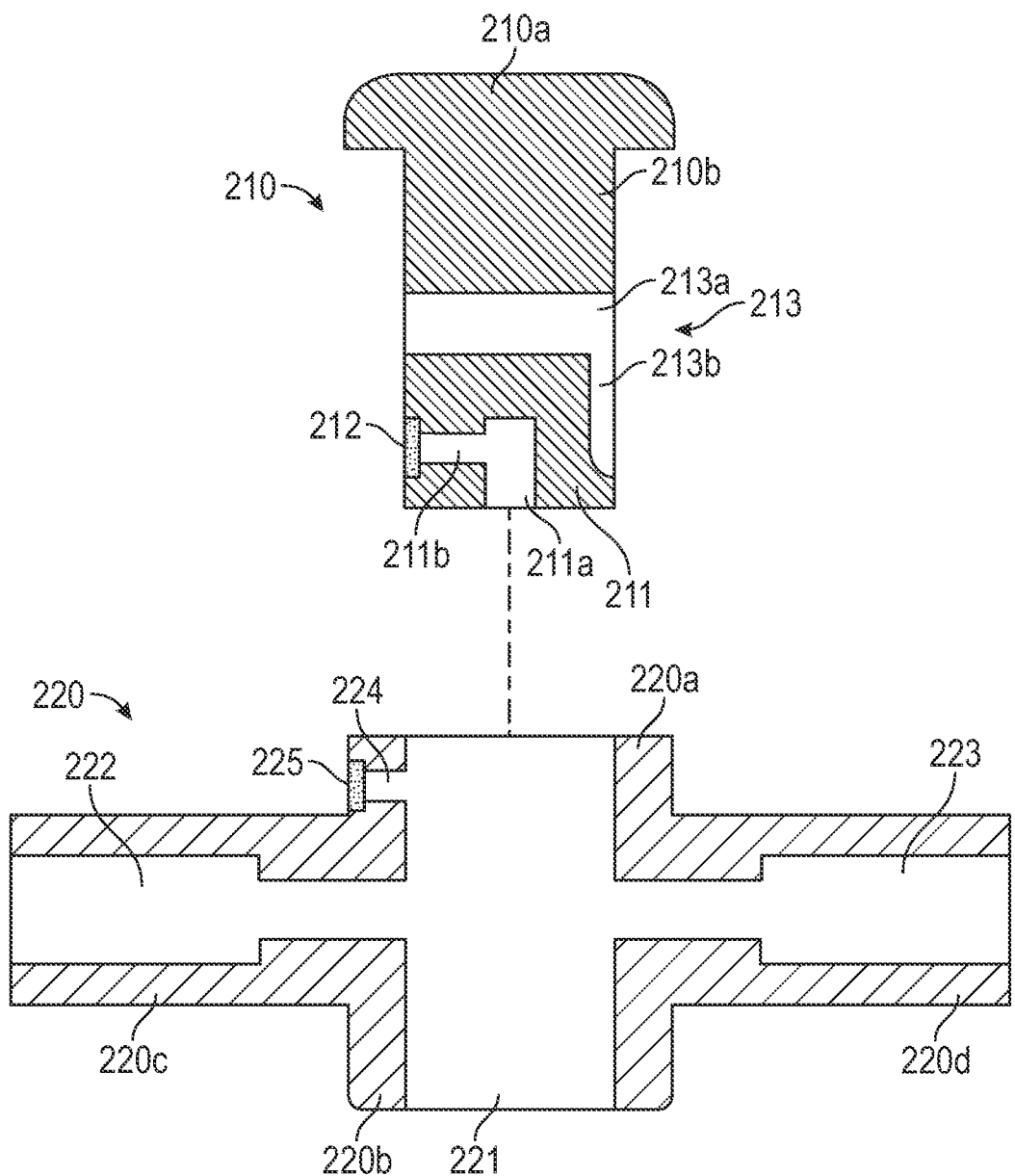
FIG. 2E provides a cross-sectional, exploded view of the primer of FIGS. 2A and 2B, in accordance with some embodiments.

As illustrated in the exploded view of FIG. 2E, in some embodiments, a plunger channel 221 may extend from top 220a to bottom 220b and allows plunger 210 to be inserted into and slide within main body 220. In some embodiments, a distal channel 222 may extend from distal end 220c and may connect to plunger channel 221. Similarly, a proximal channel 223 extends from proximal end 220d and connects to plunger channel 221. In some embodiments, such as the depicted embodiment, at least a portion of distal channel 222 and proximal channel 223 may be sized to receive and secure the respective ends of extension tubing 130. In some embodiments, main body 220 may include a venting channel 224 that extends from plunger channel 221 through an exterior surface of main body 220. In some embodiments, a first venting member 225 may be positioned within venting channel 224 and may be configured to allow air, but not fluid, to escape from venting channel 224. In some embodiments, first venting member 225 may be a hydrophobic membrane.

In some embodiments, plunger 210 may include an actuating member 210a and a plunger main body 210b that extends downwardly from actuating member 210a. In some embodiments, plunger main body 210b may be sized to insert tightly into plunger channel 221 and may be formed of a material that forms a fluid-tight seal against the sidewalls of plunger channel 221.

As is best seen in the exploded view of FIG. 2E, in some embodiments, plunger main body 210b may include a first channel 213 that consists of a primary channel 213a and a branch channel 213b. In some embodiments, primary channel 213a may extend fully through plunger main body 210b from a distal side to a proximal side, while branch channel 213b extends from the proximal side of plunger main body 210b at a position below primary channel 213a up to primary channel 213a. In some embodiments, when primer 200 is in the closed position, the proximal end of branch channel 213b may be aligned with proximal channel 223, and the distal end of primary channel 213a is aligned with venting channel 224. Accordingly, in some embodiments, as represented in FIG. 2C, when priming fluid (e.g., saline) is injected into the portion of extension tubing 130 that is connected to proximal end 220d of main body 220, air contained in this portion of extension tubing 130 may flow through proximal channel 223, branch channel 213b, primary channel 213a and venting channel 224 before being vented to the exterior environment through first venting member 225. In some embodiments, this venting of air may continue until the priming fluid has flowed up to first venting member 225 and caused all air to be vented from extension tubing 130 and primer 200.

In some embodiments, plunger main body 210b may include a second channel 211 that is isolated from first channel 213. In some embodiments, second channel 211 may include a vertical channel 211a and a horizontal channel 211b. In some embodiments, vertical channel 211a may extend upwardly from a bottom of plunger main body 210b. In some embodiments, horizontal channel 211b extends from the distal side of plunger main body 210b to vertical channel 211a. In some embodiments, a second venting member 212 is positioned within second channel 211 such as at the distal end of horizontal channel 211b. In some embodiments, second venting member 212 may be in the form of a hydrophobic membrane.

In some embodiments, when primer 200 is in the closed position, horizontal channel 211b may align with distal channel 222. Accordingly, in some embodiments, as represented in FIG. 2C, as blood flows into the portion of extension tubing 130 that is distal to primer 200, air contained in this portion of extension tubing 130 may pass through second venting member 212 and vent through second channel 211 and plunger channel 221 into the external environment.

As may be seen from FIG. 2C, in some embodiments, primer 200 may vent air from both the distal and proximal portions of extension tubing 130 to thereby allow blood and priming fluid to flow into primer 200. In some embodiments, the configuration of first channel 213 and second channel 211 may maintain isolation between the blood and priming fluid while primer 200 remains in the closed position. More particularly, in some embodiments, the configuration of branch channel 213b relative to proximal channel 223 and the configuration of primary channel 213a relative to venting channel 224 may form a fluid pathway from the proximal portion of extension tubing 130 up to first venting member 225. Likewise, in some embodiments, the configuration of second channel 211 and the position of second venting member 212 may form a separate fluid pathway from the distal portion of extension tubing 130 up to second venting member 212.

In some embodiments, in response to the flow of blood forcing all air out through second venting member 212 and the flow of priming fluid forcing all air out through first venting member 225, integrated PIVC 100 may be fully primed while maintaining isolation between the blood and the priming fluid. In some embodiments, at this point, primer 200 may be transitioned into the open position represented in FIGS. 2B and 2D by applying a force on actuating member 210a. For example, a clinician may place his or her thumb on actuating member 210a and place his or her fingers under distal end 220c and proximal end 220d and then provide a squeezing force.

In some embodiments, in the open position, primary channel 213a may align with both proximal channel 223 and distal channel 222 thereby opening a fluid pathway through primer 200. In some embodiments, the priming fluid that has filled proximal channel 223 may commence flowing through proximal channel 223 and into distal channel 222 causing the blood to be flushed towards the patient's vasculature.

Figure 3:
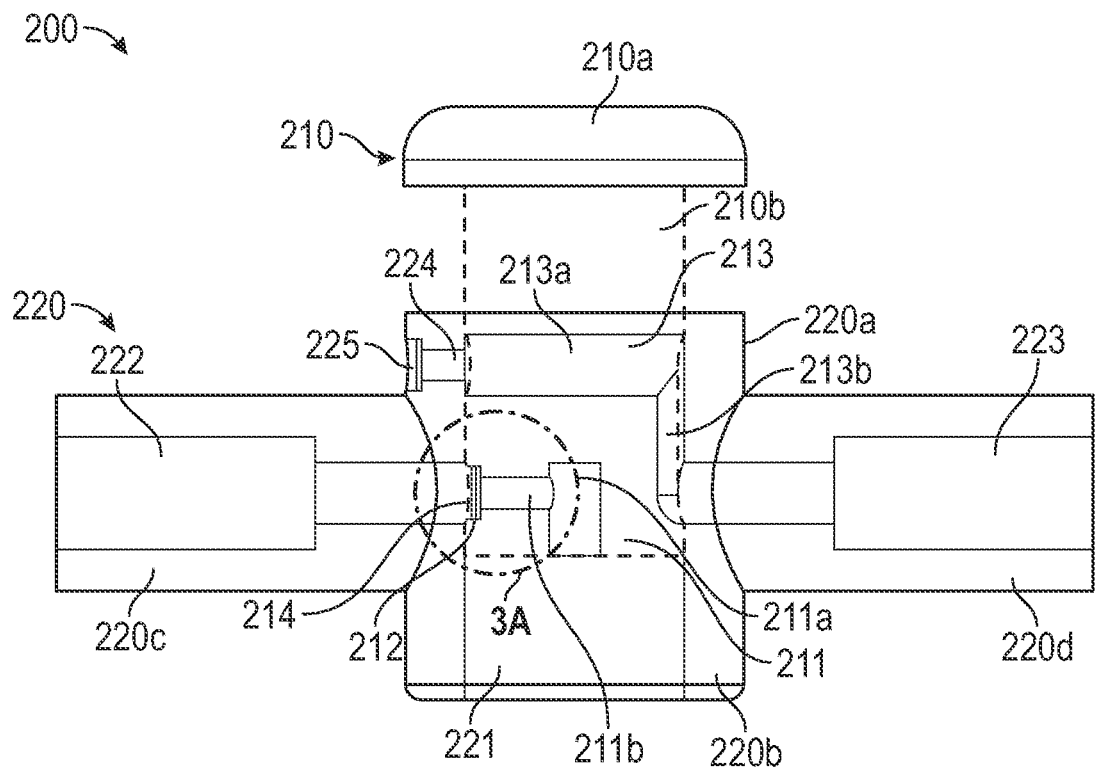
FIGS. 3 and 3A are front views of the primer of FIGS. 2A and 2B, illustrating an example a hydrophilic membrane, in accordance with some embodiments.
Figure 3A:
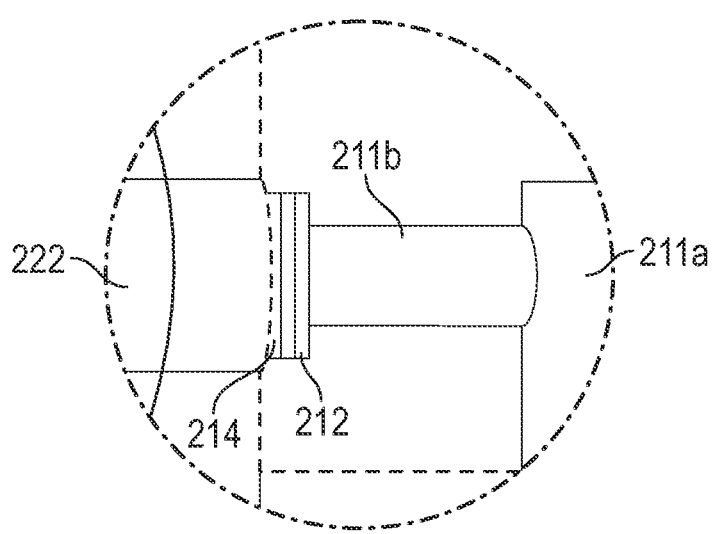

In some embodiments, such as is represented in FIGS. 3 and 3A, a hydrophilic membrane 214 may be positioned distal to second venting member 212 so that hydrophilic membrane 214 will be exposed to the blood that flows into distal channel 222. In some embodiments, hydrophilic membrane 214 may absorb the blood and eventually form an air barrier to prevent air from passing back through second venting member 212 and into distal channel 222.

In some embodiments, primer 200 may be configured in this manner when it is intended to be used on an integrated catheter system that is configured to enable blood to be drawn from catheter adapter 121 or any other component that is distal to primer 200. In such cases, as blood is drawn, a vacuum may be created distal to primer 200. In some embodiments, absent hydrophilic membrane 214, this vacuum could cause air to pass distally through second venting member 212 (e.g., through a hydrophobic membrane) and into distal channel 222. However, in some embodiments, with hydrophilic membrane 214, air may initially be vented proximally through hydrophilic membrane 214 and second venting member (or hydrophobic membrane) 212 until hydrophilic membrane 214 absorbs blood at which point air will no longer pass through hydrophilic membrane 214. In some embodiments, at that point, if a vacuum is created as blood is drawn from a point distal to primer 200, hydrophilic membrane 214 will block the flow of air towards the vacuum thus maintaining the primed state of the portion of the catheter system distal to primer 200.

Figure 4C:
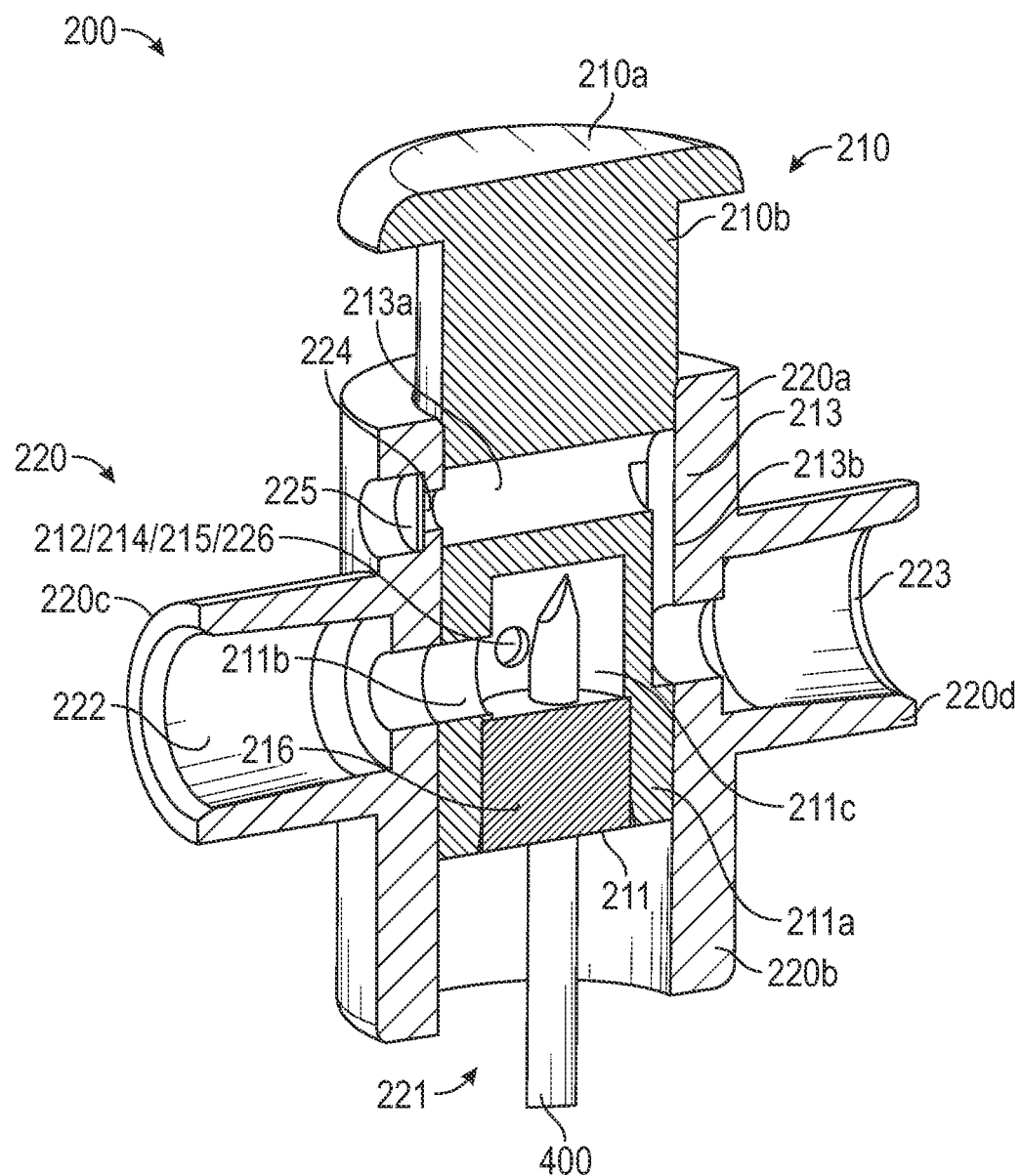
FIG. 4C is a cross-sectional view of the primer of FIG. 4A when a needle of a blood collection set has been inserted into the primer, in accordance with some embodiments.
Figure 4D:
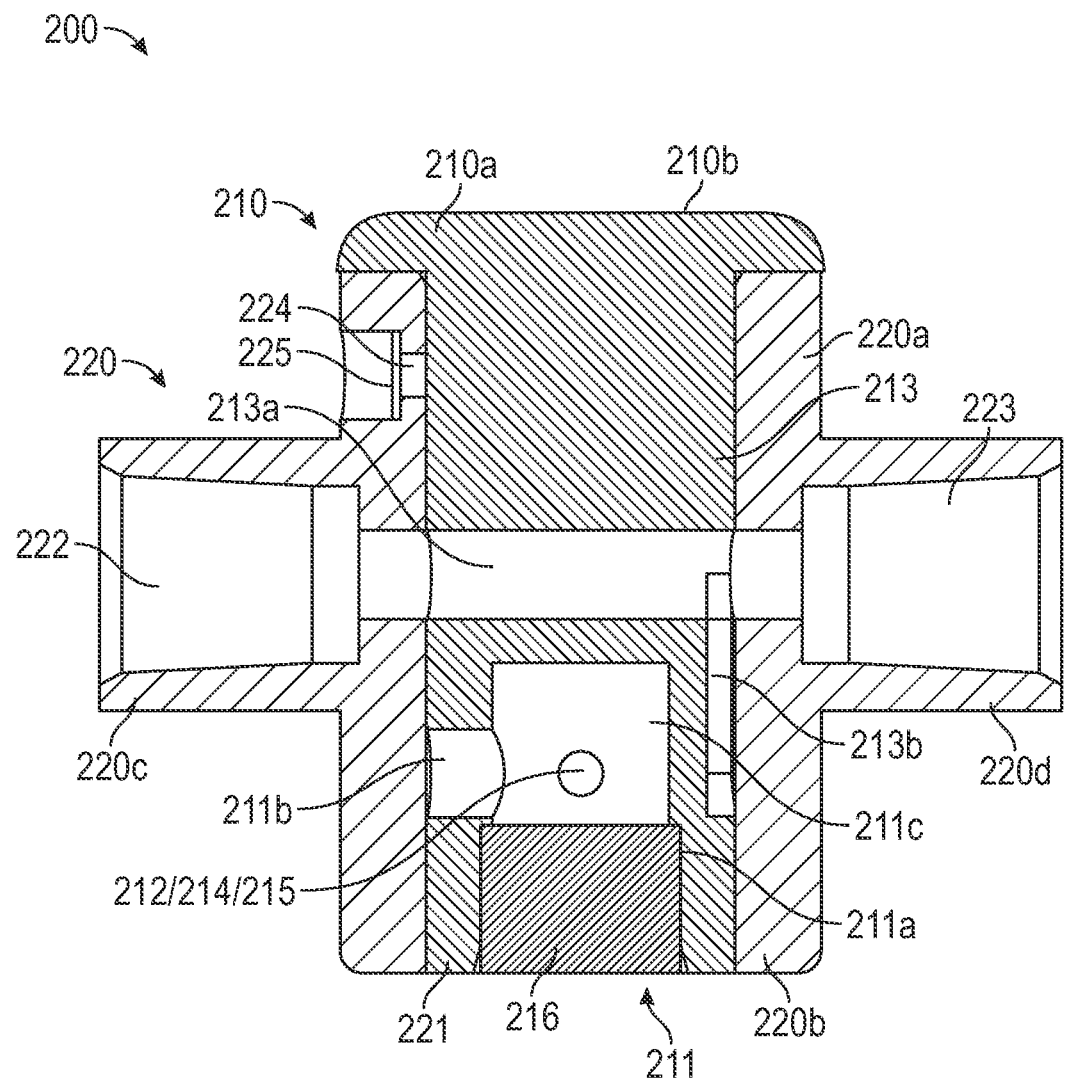
FIG. 4D is a cross-sectional view of the primer of FIG. 4A when the primer is in the open position, in accordance with some embodiments.

In some embodiments, primer 200 may be configured to enable a blood sample to be drawn from second channel 211. FIGS. 4A-4D are examples of such embodiments. FIG. 4A provides a transparent front view of primer 200 in the closed position, FIG. 4B provides a cross-sectional side view of primer 200 in the closed position, FIG. 4C provides a cross-sectional perspective view of primer 200 in the closed position during a blood draw and FIG. 4D provides a cross-sectional front view of primer 200 in the open position.

In these embodiments, main body 220 may be configured in the same or similar manner as described above except that a second venting channel 226 may extend from plunger channel 221 through an exterior surface of main body 220. With reference to FIG. 4A, in some embodiments, second venting channel 226 extends rearwardly but could also extend frontwardly or in any other direction that causes it to pass through the exterior surface of main body 220.

In these embodiments, plunger 210 may also have a similar design as described above except that a septum 216 is positioned in and seals vertical channel 211a and second channel 211 includes a blood chamber 211c to which vertical channel 211a and horizontal channel 211b are connected. As best seen in FIG. 4B, in some embodiments, plunger main body 210b may include a third channel 215 within which second venting member 212 and possibly hydrophilic membrane 214 are positioned. In some embodiments, third channel 215 may extend from blood chamber 211c through the exterior surface of plunger main body 210b at a point that aligns with second venting channel 226 when primer 200 is in the closed position. Accordingly, in some embodiments, in response to the catheter being placed in the patient's vasculature, blood may flow towards primer 200 due to the venting of air through third channel 215 and second venting channel 226.

In some embodiments, blood chamber 211c may function to collect blood and form an area from which blood may be drawn. For example, FIG. 4C illustrates that a needle 400 of a blood collection set (not shown) has been inserted into plunger channel 221 and through septum 216 so that its tip is positioned within blood chamber 211c. In some embodiments, in response to needle 400 in this position, a blood sample may be obtained. In some embodiments, in the same manner as described above, hydrophilic membrane 214 may function as an air barrier to prevent air from passing from the exterior environment into blood chamber 211c due to any vacuum that the blood collection set may create during the blood draw.

In some embodiments, after collecting a blood sample, or, if no blood sample is collected, after primer 200 has caused both sides of the catheter system to become primed, primer 200 may be transitioned into the open position as shown in FIG. 4D. In this open position, primer 200 may function in the same manner as described above.

In some embodiments, notably, due to its configuration, when primer 200 is in the open position, first venting member 225 and second venting member 212 may be isolated from the fluid pathway (i.e., isolated from primary channel 213a). This renders primer 200 capable of supporting power injection. In particular, in some embodiments, the interface between plunger main body 210b and the sidewall of plunger channel 221 will form a seal that isolates these venting members, which may otherwise be damaged during power injection, from the fluid pathway where the power injection is performed. Also, in some embodiments, because primary channel 213a passes straight through plunger main body 210b and aligns with distal channel 222 and proximal channel 223, the fluid pathway through primer 200 may be straight thereby reducing or eliminating any pressure drop through primer 200.

All examples and conditional language recited herein are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed:

1. A primer for an intravenous catheter system, comprising:
   a main body forming a plunger channel and having a distal end that forms a distal channel that connects to the plunger channel and a proximal end that forms a proximal channel that connects to the plunger channel, the main body further having a venting channel that extends between the plunger channel through an exterior surface of the main body; and
   a plunger having a plunger main body that inserts into and slides within the plunger channel between a closed position and an open position, the plunger main body having a first channel and a second channel;
   wherein, in response to the plunger being in the closed position, the first channel connects the proximal channel to the venting channel to thereby vent air contained in extension tubing connected to the proximal end through the venting channel, and the second channel is aligned with the distal channel to thereby vent air contained in extension tubing connected to the distal end through the second channel;
   wherein, in response to the plunger being in the open position, the first channel connects the proximal channel to the distal channel to thereby enable fluid flow through the primer.

2. The primer of claim 1, wherein the first channel comprises a primary channel that extends through the plunger main body and a branch channel that extends from the primary channel through a proximal exterior surface of the plunger main body.

3. The primer of claim 2, wherein, in response to the plunger being in the closed position, the branch channel aligns with the proximal channel and the primary channel aligns with the venting channel.

4. The primer of claim 3, wherein, in response to the plunger being in the open position, the primary channel aligns with the proximal channel and the distal channel.

5. The primer of claim 1, wherein the second channel comprises a horizontal channel that extends through a distal exterior surface of the plunger main body and a vertical channel that extends through a bottom exterior surface of the plunger main body.

6. The primer of claim 5, wherein, in response to the plunger being in the closed position, the horizontal channel aligns with the distal channel.

7. The primer of claim 1, further comprising:
   a first venting member positioned in the venting channel; and
   a second venting member positioned in the second channel.

8. The primer of claim 7, wherein the first and second venting members are each hydrophobic membranes, the primer further comprising:
   a hydrophilic membrane positioned in the second channel distal to the second venting member.

9. The primer of claim 1, wherein the plunger further comprises an actuating member connected to the plunger main body.

10. The primer of claim 1, wherein the main body further comprises a second venting channel that extends from the plunger channel through the exterior surface of the main body, the second channel forms a blood chamber and the plunger main body further comprises a third channel that extends from the blood chamber through an exterior surface of the plunger main body;

wherein, in response to the plunger being in the closed position, the third channel aligns with the second venting channel such that the air contained in the extension tubing connected to the distal end is vented through the second channel, the third channel and the second venting channel.

11. The primer of claim 10, wherein the second channel comprises a horizontal channel that extends through a distal exterior surface of the plunger main body and a vertical channel that extends through a bottom exterior surface of the plunger main body, the blood chamber being formed between the horizontal and vertical channels, the primer further comprising:
a septum positioned in the vertical channel between the blood chamber and the bottom exterior surface.

12. The primer of claim 10, further comprising:
a first venting member positioned in the venting channel; and
a second venting member positioned in the third channel.

13. The primer of claim 12, wherein the first and second venting members are each hydrophobic membranes, the primer further comprising:
a hydrophilic membrane positioned in the third channel between the second venting member and the blood chamber.

14. An intravenous catheter system comprising:
a catheter assembly having a catheter adapter and a catheter that extends distally from the catheter adapter;
extension tubing that is fluidly coupled to the catheter adapter;
an access port positioned at a proximal end of the extension tubing; and
a primer that is connected inline to the extension tubing such that a distal portion of the extension tubing is positioned between the primer and the catheter adapter and a proximal portion of the extension tubing is positioned between the primer and the access port, the primer comprising:
a main body forming a plunger channel and having a distal end that is coupled to the distal portion of the extension tubing, the distal end forming a distal channel that connects to the plunger channel, the main body also having a proximal end that is coupled to the proximal portion of the extension tubing, the proximal end forming a proximal channel that connects to the plunger channel, the main body further having a venting channel that extends between the plunger channel through an exterior surface of the main body; and
a plunger having a plunger main body that inserts into and slides within the plunger channel between a closed position and an open position, the plunger main body having a first channel and a second channel;
wherein, in response to the plunger being in the closed position, the first channel connects the proximal channel to the venting channel to thereby vent air contained in the proximal portion of the extension tubing through the venting channel, and the second channel is aligned with the distal channel to thereby vent air contained in distal portion of the extension tubing through the second channel;
wherein, in response to the plunger being in the open position, the first channel connects the proximal channel to the distal channel to thereby enable fluid flow through the primer.

15. The intravenous catheter system of claim 14, wherein the first channel comprises a primary channel that extends through the plunger main body and a branch channel that extends from the primary channel through a proximal exterior surface of the plunger main body;
wherein, in response to the plunger being in the closed position, the branch channel aligns with the proximal channel and the primary channel aligns with the venting channel;
wherein, in response to the plunger being in the open position, the primary channel aligns with the proximal channel and the distal channel.

16. The intravenous catheter system of claim 14, wherein the second channel comprises a horizontal channel that extends through a distal exterior surface of the plunger main body and a vertical channel that extends through a bottom exterior surface of the plunger main body.

17. The intravenous catheter system of claim 14, wherein the main body further comprises a second venting channel that extends from the plunger channel through the exterior surface of the main body, the second channel forms a blood chamber and the plunger main body further comprises a third channel that extends from the blood chamber through an exterior surface of the plunger main body;
wherein, in response to the plunger being in the closed position, the third channel aligns with the second venting channel such that the air contained in the distal portion of the extension tubing is vented through the second channel, the third channel and the second venting channel.

18. The intravenous catheter system of claim 17, wherein the primer comprises:
a septum positioned in the second channel between the blood chamber and a bottom exterior surface of the plunger main body.

19. The intravenous catheter system of claim 14, further comprising:
a first venting member that vents the air contained in the proximal portion of the extension tubing;
a second venting member that vents the air contained in the distal portion of the extension tubing; and
a hydrophilic membrane that is positioned distal to the second venting member.

20. A primer for an intravenous catheter system comprising:
a main body forming a plunger channel and having a distal end that forms a distal channel that connects to the plunger channel and a proximal end that forms a proximal channel that connects to the plunger channel, the main body further having a venting channel that extends between the plunger channel through an exterior surface of the main body; and
a plunger having a plunger main body that inserts into and slides within the plunger channel between a closed position and an open position, the plunger main body having a first channel and a second channel, the first channel comprising a primary channel and a branch channel;
wherein, in response to the plunger being in the closed position, the branch channel aligns with the proximal channel and the primary channel aligns with the venting channel to thereby vent air contained in extension tubing connected to the proximal end through the venting channel, and the second channel is aligned with the distal channel to thereby vent air contained in extension tubing connected to the distal end through the second channel;

wherein, in response to the plunger being in the open position, the primary channel connects the proximal channel to the distal channel to thereby enable fluid flow through the primer.

\* \* \* \* \*